United States Patent
Mazor et al.

[11] Patent Number: 6,108,398
[45] Date of Patent: Aug. 22, 2000

[54] X-RAY MICROFLUORESCENCE ANALYZER

[75] Inventors: Isaac Mazor, Denia Haifa; Amos Gvirtzman, Zippori; Boris Yokhin, Nazareth Illit, all of Israel

[73] Assignee: Jordan Valley Applied Radiation Ltd., Migdal Ha'emek, Israel

[21] Appl. No.: 09/114,789

[22] Filed: Jul. 13, 1998

[51] Int. Cl.$^7$ .............................................. G01N 23/223
[52] U.S. Cl. .............................................. 378/45; 379/49
[58] Field of Search .................. 378/44, 45, 50, 378/49

[56] References Cited

U.S. PATENT DOCUMENTS

| | | | |
|---|---|---|---|
| 3,256,431 | 6/1966 | Fraser | 378/47 |
| 3,581,087 | 5/1971 | Brinkerhoff | 378/45 |
| 3,980,568 | 9/1976 | Pitchford et al. | 378/49 |
| 4,852,135 | 7/1989 | Anisovich et al. | 378/49 |
| 5,497,008 | 3/1996 | Kumakhov | 250/505.1 |
| 5,778,039 | 7/1998 | Hossain et al. | 378/44 |
| 5,937,026 | 8/1999 | Satoh | 378/44 |

OTHER PUBLICATIONS

S. Shimomura et al., "Annular–Type Solid State Detector for a Scanning X–Ray Analytical Microscope", *Rev. Sci. Instrum.* vol. 66(9), pp. 4544–4546 (Sep. 1995).

B. J. Cross et al., "X–Ray Microfluorescence Analyzer for Multilayer Metal Films", *Thin Solid Films*, vol. 166, pp. 263–272 (1988).

N. Yamamoto, "A Micro–Fluorescent/Diffracted X–Ray Spectrometer with a Micro–X–Ray Beam Formed by a Fine Glass Capillary", *Rev. Sci. Instrum.*, vol. 67(9), pp. 3051, 3054–3056, 3062 (Sep. 1996).

*Brochure*: Capillary Optics, by X–Ray Capillary Optics AB, Sweden (1995).

*Primary Examiner*—David P. Porta
*Assistant Examiner*—Drew A. Dunn
*Attorney, Agent, or Firm*—Lahive & Cockfield, LLP

[57] ABSTRACT

An x-ray fluorescent analyzer and method for analyzing a sample, including an x-ray beam generator, which generates an x-ray beam incident at a spot on the sample, and creates a plurality of fluorescent x-ray photons. There are a plurality of semiconducting detectors arrayed around the spot so as to capture the fluorescent x-ray photons and in response produce a plurality of electrical pulses suitable for analysis of the sample.

13 Claims, 1 Drawing Sheet

X-RAY MICROFLUORESCENCE ANALYZER

FIELD OF THE INVENTION

The present invention relates generally to x-ray fluorescence analysis, and specfically to methods and devices to detect and analyze x-ray microfluorescence.

BACKGROUND OF THE INVENTION

X-ray microfluorescence is a non-destructive technique known in the art for determining the atomic composition and thickness of thin films. Typically, a focused x-ray beam is directed at a sample, and the x-ray fluorescence induced by the interaction of the x-rays with the sample is detected by a detector located near the sample. The composition and thickness of the irradiated sample are determined from the intensity and energy of the fluorescent x-ray photons.

In "Annular-type solid state detector for a scanning x-ray analytical microscope," Rev. Sci. Instrum. 66(9) (September, 1995), pp. 4544–4546, which is incorporated herein by reference, Shimomura and Nakazawa describe an annular germanium detector located near an irradiated sample which transduces the energy resulting from x-ray fluorescence into a single channel of data.

In the article, "X-ray microfluorescence analyzer for multilayer metal films," Thin Solid Films 166 (1988), pp. 263–272, which is incorporated herein by reference, Cross and Wherry describe a system wherein a lithiumdoped silicon crystal detector captures photons emitted from a sample exposed to x-rays.

U.S. Pat. No. 5,497,008, to Kumakhov, which is incorporated herein by reference, describes analytic instruments using a polycapillary x-ray optic, also known as a Kumakhov lens, for x-ray fluorescence analysis or spectroscopy. The instruments described use a single fluorescence detector.

A single x-ray photon produces many electron-hole pairs in a semiconducting detector, and analysis of the associated current pulse shape enables the detector to measure the x-ray photon energy. However, semiconducting x-ray detectors, such as the detectors described above, are subject to "pile-up" of data, which occurs when the x-ray photons are temporally too close together for satisfactory discrimination of the current pulses created.

SUMMARY OF THE INVENTION

It is an object of some aspects of the present invention to provide improved devices and methods for performing x-ray microfluorescence analysis.

It is a further object of some aspects of the present invention to provide improved devices and methods for efficient detection of x-ray microfluorescence from a sample exposed to high intensity x-ray illumination.

In preferred embodiments of the present invention, an x-ray microfluorescence analyzer comprises an x-ray generator which irradiates a sample, and a plurality of individual detectors arrayed near the sample which capture x-ray photons emitted from the sample responsive to the x-ray illumination. The detectors are geometrically arrayed so as to capture emitted x-ray photons over a substantially larger solid angle than would be possible with a single detector of standard design, such as that of Cross and Wherry described hereinabove. Furthermore, unlike the system of Shimomura and Nakazawa, described hereinabove, based on a single large detector, the use of multiple detectors according to some embodiments of the present invention enables the analyzer to direct a substantially more intense x-ray beam at the sample, while greatly reducing the probability of pile-up occurring.

In some preferred embodiments of the present invention, the plurality of individual detectors are arranged in a ring, so that the angle created by the incident x-ray beam direction and the direction from a detector to the irradiated spot is substantially the same for all detectors. Preferably, the ring is generally centered over the irradiated spot.

The present invention will be more fully understood from the following detailed description of the preferred embodiments thereof, taken together with the drawings, in which:

DETAILED DESCRIPTION OF A PREFERRED EMBODIMENT

Figure 1A:
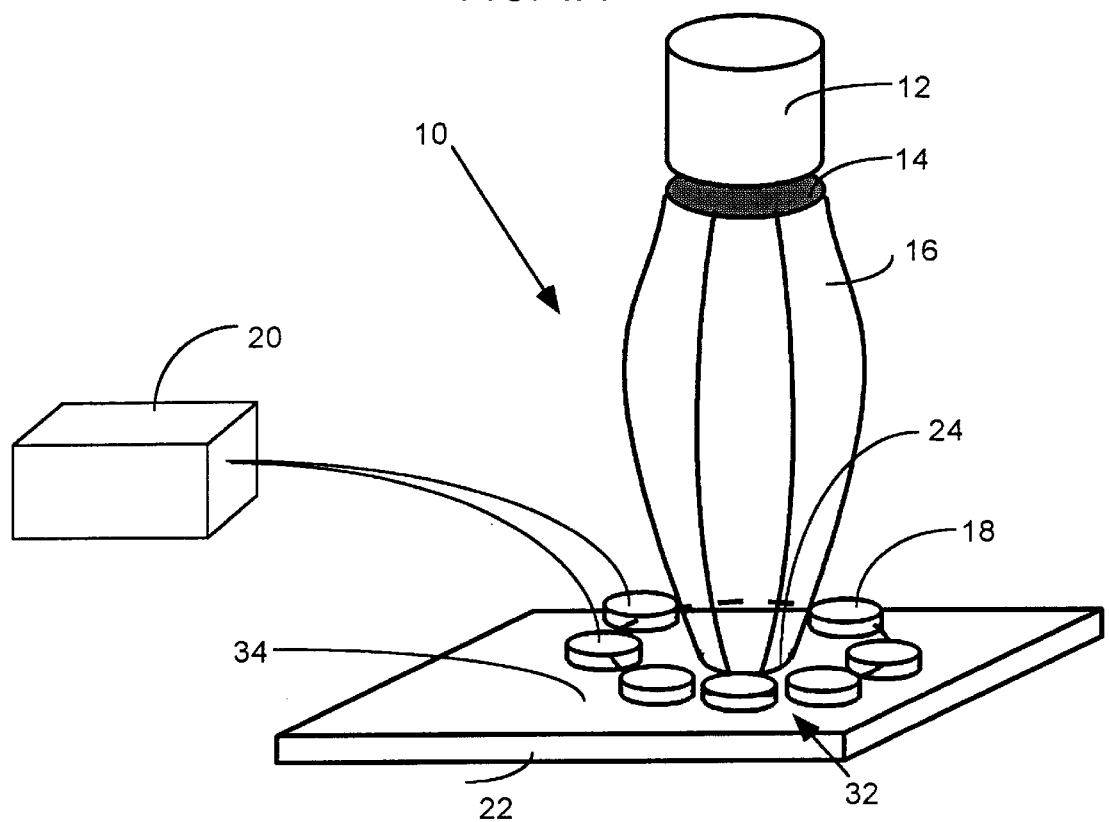
FIG. 1A is a schematic perspective view of an x-ray microfluorescence analyzer, in accordance with a preferred embodiment of the present invention.
Figure 1B:
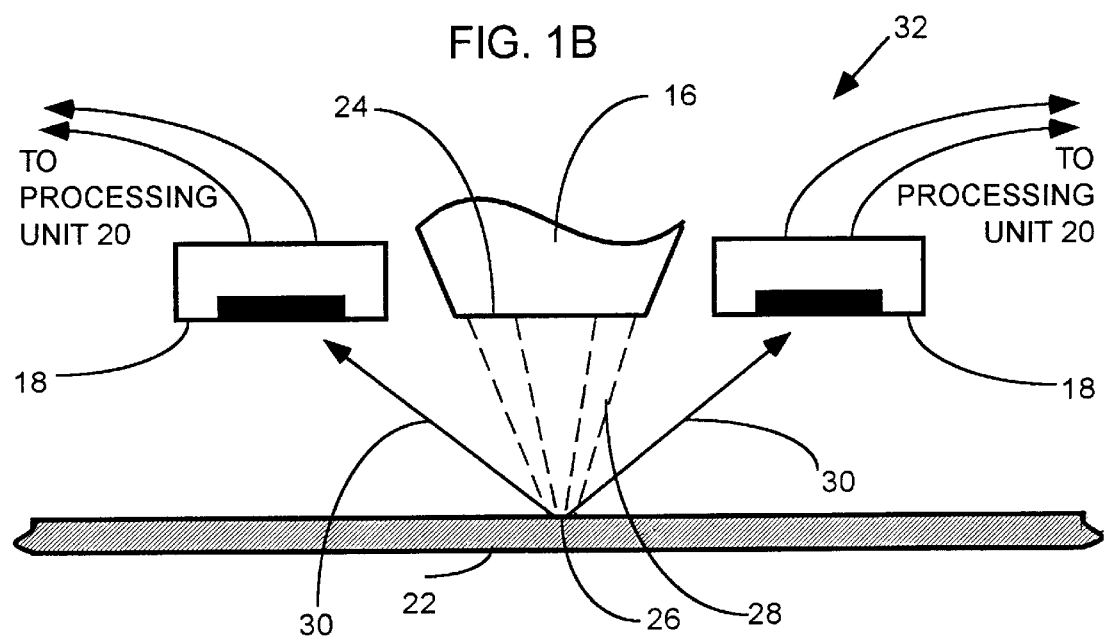
FIG. 1B is a schematic enlarged side view of a detail of the analyzer of FIG. 1A.

FIG. 1A is a schematic perspective view of an x-ray microfluorescence analyzer 10, in accordance with a preferred embodiment of the present invention. FIG. 1B is a schematic enlarged cross-sectional view of a base portion 32 of analyzer 10.

An x-ray source 12 irradiates a monolithic polycapillary optic 16 at a first end 14. X-ray source 12 preferably comprises an x-ray tube, such as an XTF 5011 produced by Oxford Instruments, Inc., of Scotts Valley, Calif. Optic 16 is preferably a monolithic polycapillary lens produced by X-Ray Optical Systems, Inc., of Albany, New York. The optic collects the x-rays, and focuses them from a second end 24 of optic 16 into a cone 28 to a spot 26. Most preferably, spot 26 is substantially circular with a diameter of the order of 50 $\mu$m. Alternatively, spot 26 is irradiated via a monocapillary optic and/or x-ray collimating pinholes, or by any other suitable means known in the art.

Most preferably, spot 26 is on a surface of a sample 22 whose composition and/or thickness is to be measured by analyzer 10. Fluorescent x-rays, emitted by sample 22 in response to the irradiating x-rays, are produced within spot 26, and are collected by a plurality of, preferably eight, detectors 18. The arrangement and operation of detectors 18 are described in more detail hereinbelow. Signals from detectors 18 are transferred to a processing unit 20, wherein the signals are analyzed to generate composition and thickness information for spot 26. Most preferably, the signals from detectors 18 are transferred via a plurality of pulse processors, and processing unit 20 comprises a multiple-input processor analyzing unit. Preferably sample 22 is scanned in horizontal directions by positioning equipment (not shown), as is known in the art, so that substantially a whole area of interest 34 of sample 22 is analyzed by analyzer 10. Alternatively analyzer 10 is scanned over area of interest 34. Most preferably the scanning is controlled by processing unit 20.

Preferably, detectors 18 are PIN diodes arranged in a circle, centered over spot 26, of diameter approximately equal to 9 mm and at a distance approximately equal to 4 mm from the surface of sample 22. Most preferably, each of the detectors have an active collection area in the form of a square of side 2.5 mm. For example, the detectors are type S1223 produced by Hamamatsu Photonics, K. K., of Hamamatsu City, Japan. It will be appreciated that the number and type of detectors and their dimensions and positions cited above are given by way of example, and other numbers, sizes, types and positions may similarly be used. It will also be appreciated that while detectors 18 are shown as facing perpendicularly downwards, they may also be angled towards spot 26, in order to increase the active area presented to the spot.

During irradiation by cone 28, spot 26 generates fluorescent x-ray photons 30 which are incident on detectors 18, wherein corresponding pulses are in turn generated in the detectors and conveyed to processing unit 20. The processing unit analyzes and counts the pulses from the plurality of detectors 18. Most preferably, base portion 32 of analyzer 10 is maintained substantially stationary over spot 26 until sufficient counts have been recorded by unit 20 for a satisfactory determination of the composition and thickness of spot 26. Processing unit 20 then moves either sample 22 or base portion 32, as described above, to a new spot 26 to be analyzed.

The amount of time analyzer 10 needs to spend over a spot 26 is dependent, inter alia, on the intensity of irradiating x-rays at spot 26. The intensity of irradiating x-rays using the present invention can be substantially higher than analyzers at present known in the art, before pile-up of pulses in the detectors occurs, since the pulses are received from each detector 18 individually, rather than from a single large detector. In addition, and of importance when the irradiating x-ray intensity is a limiting factor, for example when higher intensities might cause damage, the present invention increases the ratio of the useful number of photons out to the number of photons in. Thus, a relatively large number of photons may be collected in a relatively short time, so that the time required for analysis of a spot 26 is correspondingly reduced relative to systems known in the art.

It will be appreciated that the preferred embodiments described above are cited by way of example, and the full scope of the invention is limited only by the claims.

What is claimed is:

1. An x-ray fluorescent analyzer for analyzing a sample, comprising:

an x-ray beam generator, which generates an x-ray beam incident at a spot on the sample, creating therefrom a plurality of fluorescent x-ray photons;

a plurality of semiconducting detectors arrayed around the spot so as to capture the fluorescent x-ray photons within an energy range common to all of the detectors, and responsive thereto to produce a plurality of electrical pulses suitable for analysis of the sample; and a multiple-input processing unit which receives and analyzes the plurality of pulses, such that the pulses from each of the detectors are received at a separate input of the processing unit, and which generates an output using the pulses received from all of the detectors responsive to the photons within the energy range common to all of the detectors.

2. An analyzer according to claim 1, wherein the x-ray generator comprises a capillary optic.

3. An analyzer according to claim 2, wherein the capillary optic comprises a polycapillary optic.

4. An analyzer according to claim 1, wherein the plurality of detectors comprises a plurality of diodes.

5. An analyzer according to claim 1, wherein the plurality of detectors are symmetrically disposed relative to a spot where the beam is incident on the sample.

6. An analyzer according to claim 5, wherein the plurality of detectors are disposed in a ring.

7. An analyzer according to claim 1, wherein the processing unit analyzes the plurality of pulses to determine a thickness or a composition of the sample.

8. A method for x-ray fluorescent analysis of a sample comprising:

irradiating a spot on the sample with a beam of x-rays;

arranging a plurality of x-ray detectors around the spot so as to detect a plurality of fluorescent x-ray photons produced within an energy range common to all of the detectors by the beam interacting with the sample at the spot;

receiving from all of the detectors a plurality of electrical pulses responsive to the photons produced within the energy range common to all of the detectors; and processing the pulses received from all of the detectors responsive to the photons produced within the energy range common to all of the detectors so as to analyze the sample.

9. A method according to claim 8, wherein irradiating the sample comprises irradiating the sample using a capillary optic.

10. A method according to claim 8, wherein providing the plurality of detectors comprises providing a plurality of semiconducting diodes.

11. A method according to claim 8, wherein arranging the plurality of detectors comprises disposing the detectors generally symmetrically relative to the spot.

12. A method according to claim 11, wherein disposing the detectors comprises arranging the detectors in a ring generally centered over the spot.

13. A method according to claim 8, wherein receiving the plurality of pulses comprises separately receiving the pulses from each of the plurality of detectors.

* * * * *